(12) United States Patent
Gordon et al.

(10) Patent No.: US 10,202,117 B2
(45) Date of Patent: Feb. 12, 2019

(54) AUTOMATED SPATIAL SEPARATION OF SELF-DRIVING VEHICLES FROM OTHER VEHICLES BASED ON OCCUPANT PREFERENCES

(71) Applicant: International Business Machines Corporation, Armonk, NY (US)

(72) Inventors: Michael S. Gordon, Yorktown Heights, NY (US); James R. Kozloski, New Fairfield, CT (US); Ashish Kundu, New York, NY (US); Peter K. Malkin, Ardsley, NY (US); Clifford A. Pickover, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/807,667

(22) Filed: Nov. 9, 2017

(65) Prior Publication Data

US 2018/0065632 A1    Mar. 8, 2018

Related U.S. Application Data

(63) Continuation of application No. 14/833,652, filed on Aug. 24, 2015, now Pat. No. 9,896,100.

(51) Int. Cl.
*B60W 30/16*      (2012.01)
*B60W 40/08*      (2012.01)
(Continued)

(52) U.S. Cl.
CPC .............. *B60W 30/16* (2013.01); *A61B 5/18* (2013.01); *A61B 5/165* (2013.01); *B60W 2540/22* (2013.01); *B60W 2750/308* (2013.01)

(58) Field of Classification Search
None
See application file for complete search history.

(56) References Cited

U.S. PATENT DOCUMENTS

| 4,665,395 A | 5/1987 | Van Ness |
| 4,908,988 A | 3/1990 | Yamamura et al. |

(Continued)

FOREIGN PATENT DOCUMENTS

| CN | 1135063 | 11/1996 |
| CN | 2349068 Y | 11/1999 |

(Continued)

OTHER PUBLICATIONS

Anonymous, 'System and Method to Target Advertisements for the Right Focus Group'. ip.com, No. 000218285, May 31, 2012, pp. 1-2.

(Continued)

*Primary Examiner* — Rami Khatib
*Assistant Examiner* — Gerrad A Foster
(74) *Attorney, Agent, or Firm* — Law Office of Jim Boice

(57) ABSTRACT

A computer-implemented method, system, and/or computer program product automatically provides spatial separation between a self-driving vehicle (SDV) operating in an autonomous mode and another vehicle on a roadway. One or more processors receive an emotional state descriptor for at least one occupant of the SDV and determine an emotional state of the occupant(s) of the SDV. A vehicle detector on the SDV detects another vehicle and the size of the other vehicle within a predefined proximity of the SDV. A control mechanisms controller determines that a field of view for the occupants in the SDV is blocked by the size of the other vehicle. The processor(s) issue spatial separation instructions to the control mechanisms controller on the SDV to adjust a spacing between the SDV and the other vehicle based on the emotional state descriptor for the occupant(s) in the SDV and the field of view for the occupant(s) in the SDV that is blocked by the size of the other vehicle.

18 Claims, 8 Drawing Sheets

(51) Int. Cl.
*A61B 5/18* (2006.01)
*A61B 5/16* (2006.01)

(56) References Cited

U.S. PATENT DOCUMENTS

| | | |
|---|---|---|
| 5,975,791 A | 11/1999 | McCulloch |
| 6,064,970 A | 5/2000 | McMillian et al. |
| 6,201,318 B1 | 3/2001 | Guillory |
| 6,326,903 B1 | 12/2001 | Gross et al. |
| 6,393,362 B1 | 5/2002 | Burns |
| 6,502,035 B2 | 12/2002 | Levine |
| 6,587,043 B1 | 7/2003 | Kramer |
| 6,622,082 B1 | 9/2003 | Schmidt et al. |
| 6,731,202 B1 | 5/2004 | Klaus |
| 6,810,312 B2 | 10/2004 | Jammu et al. |
| 7,124,088 B2 | 10/2006 | Bauer et al. |
| 7,580,782 B2 | 8/2009 | Breed et al. |
| 7,769,544 B2 | 8/2010 | Blesener et al. |
| 7,877,269 B2 | 1/2011 | Bauer et al. |
| 7,894,951 B2 | 2/2011 | Norris et al. |
| 7,979,173 B2 | 7/2011 | Breed |
| 8,031,062 B2 | 10/2011 | Smith |
| 8,045,455 B1 | 10/2011 | Agronow et al. |
| 8,078,349 B1 | 12/2011 | Prada Gomez et al. |
| 8,090,598 B2 | 1/2012 | Bauer et al. |
| 8,139,109 B2 | 3/2012 | Schmiedel et al. |
| 8,140,358 B1 | 3/2012 | Ling et al. |
| 8,146,703 B2 | 4/2012 | Baumann et al. |
| 8,152,325 B2 | 4/2012 | McDermott |
| 8,180,322 B2 | 5/2012 | Lin et al. |
| 8,346,480 B2 | 1/2013 | Trepagnier et al. |
| 8,352,112 B2 | 1/2013 | Mudalige |
| 8,442,854 B2 | 5/2013 | Lawton et al. |
| 8,466,807 B2 | 6/2013 | Mudalige |
| 8,489,434 B1 | 7/2013 | Otis et al. |
| 8,583,365 B2 | 11/2013 | Jang et al. |
| 8,660,734 B2 | 2/2014 | Zhu et al. |
| 8,676,466 B2 | 3/2014 | Mudalige |
| 8,678,701 B1 | 3/2014 | Aldasem |
| 8,781,964 B2 | 7/2014 | Martin et al. |
| 8,786,461 B1 | 7/2014 | Daudelin |
| 8,816,857 B2 | 8/2014 | Nordin et al. |
| 8,874,305 B2 | 10/2014 | Dolgov et al. |
| 8,880,270 B1 | 11/2014 | Ferguson et al. |
| 8,892,451 B2 | 11/2014 | Everett |
| 8,903,591 B1 | 12/2014 | Ferguson et al. |
| 8,923,890 B1 | 12/2014 | White et al. |
| 8,928,479 B2 | 1/2015 | Gonsalves et al. |
| 8,935,034 B1 | 1/2015 | Zhu |
| 8,948,955 B2 | 2/2015 | Zhu et al. |
| 8,949,016 B1 | 2/2015 | Ferguson et al. |
| 8,954,217 B1 | 2/2015 | Montemerlo et al. |
| 8,954,252 B1 | 2/2015 | Urmson et al. |
| 8,954,261 B2 | 2/2015 | Das et al. |
| 8,958,943 B2 | 2/2015 | Bertosa et al. |
| 8,965,621 B1 | 2/2015 | Urmson et al. |
| 8,970,362 B2 | 3/2015 | Morley et al. |
| 8,983,705 B2 | 3/2015 | Zhu et al. |
| 8,996,224 B1 | 3/2015 | Herbach et al. |
| 9,014,905 B1 | 4/2015 | Kretzschmar et al. |
| 9,024,787 B2 | 5/2015 | Alshinnawi et al. |
| 9,123,049 B2 | 9/2015 | Hyde et al. |
| 9,170,327 B2 | 10/2015 | Choe et al. |
| 9,189,897 B1 | 11/2015 | Stenneth |
| 9,194,168 B1 | 11/2015 | Lu et al. |
| 9,216,745 B2 | 12/2015 | Beardsley et al. |
| 9,218,698 B2 | 12/2015 | Ricci |
| 9,286,520 B1 | 3/2016 | Lo et al. |
| 9,317,033 B2 | 4/2016 | Ibanez-Guzman et al. |
| 9,381,915 B1 | 7/2016 | Crombez et al. |
| 9,390,451 B1 | 7/2016 | Slusar |
| 9,399,472 B2 | 7/2016 | Minoiu-Enache |
| 9,463,805 B2 | 10/2016 | Kirsch et al. |
| 9,483,948 B1 | 11/2016 | Gordon et al. |
| 9,552,735 B2 | 1/2017 | Pilutti et al. |
| 9,566,958 B2 | 2/2017 | Waldmann |
| 9,566,986 B1 | 2/2017 | Gordon et al. |
| 9,587,952 B1 | 3/2017 | Slusar |
| 9,628,975 B1 | 4/2017 | Watkins et al. |
| 9,646,496 B1 | 5/2017 | Miller |
| 9,718,468 B2 | 8/2017 | Barfield et al. |
| 9,834,224 B2 | 12/2017 | Gordon et al. |
| 2002/0026841 A1 | 3/2002 | Svendsen |
| 2003/0065572 A1 | 4/2003 | McNee et al. |
| 2003/0076981 A1 | 4/2003 | Smith et al. |
| 2004/0078133 A1 | 4/2004 | Miller |
| 2004/0117086 A1 | 6/2004 | Rao et al. |
| 2004/0199306 A1 | 10/2004 | Heilmann et al. |
| 2005/0104745 A1 | 5/2005 | Bachelder et al. |
| 2006/0106671 A1 | 5/2006 | Biet |
| 2006/0163939 A1 | 7/2006 | Kuramochi et al. |
| 2006/0200379 A1 | 9/2006 | Biet |
| 2006/0241855 A1 | 10/2006 | Joe et al. |
| 2007/0100687 A1 | 5/2007 | Yoshikawa |
| 2007/0124027 A1 | 5/2007 | Betzitza et al. |
| 2008/0048850 A1 | 2/2008 | Yamada |
| 2008/0114663 A1 | 5/2008 | Watkins et al. |
| 2008/0129475 A1 | 6/2008 | Breed et al. |
| 2008/0201217 A1 | 8/2008 | Bader et al. |
| 2008/0288406 A1 | 11/2008 | Seguin et al. |
| 2009/0094109 A1 | 4/2009 | Aaronson et al. |
| 2009/0248231 A1 | 10/2009 | Kamiya |
| 2009/0313096 A1 | 12/2009 | Kama |
| 2010/0057511 A1 | 3/2010 | Mansouri et al. |
| 2010/0156672 A1 | 6/2010 | Yoo et al. |
| 2010/0179720 A1 | 7/2010 | Lin et al. |
| 2010/0228427 A1 | 9/2010 | Anderson et al. |
| 2010/0256852 A1 | 10/2010 | Mudalige |
| 2011/0029173 A1 | 2/2011 | Hyde et al. |
| 2011/0035250 A1 | 2/2011 | Finucan |
| 2011/0077807 A1 | 3/2011 | Hyde et al. |
| 2011/0077808 A1 | 3/2011 | Hyde et al. |
| 2011/0137699 A1 | 6/2011 | Ben-Ari et al. |
| 2011/0264521 A1 | 10/2011 | Straka |
| 2012/0072243 A1 | 3/2012 | Collins et al. |
| 2012/0083960 A1 | 4/2012 | Zhu |
| 2012/0139756 A1 | 6/2012 | Djurkovic |
| 2012/0277947 A1 | 11/2012 | Boehringer et al. |
| 2013/0030657 A1 | 1/2013 | Chatterjee et al. |
| 2013/0113634 A1 | 5/2013 | Hutchinson et al. |
| 2013/0131949 A1 | 5/2013 | Shida |
| 2013/0144502 A1 | 6/2013 | Shida |
| 2013/0231824 A1 | 9/2013 | Wilson et al. |
| 2013/0261871 A1 | 10/2013 | Hobbs et al. |
| 2014/0019259 A1 | 1/2014 | Dung et al. |
| 2014/0032049 A1 | 1/2014 | Moshchuk et al. |
| 2014/0088850 A1 | 3/2014 | Schuberth |
| 2014/0092332 A1 | 4/2014 | Price |
| 2014/0095214 A1 | 4/2014 | Mathe et al. |
| 2014/0129073 A1 | 5/2014 | Ferguson |
| 2014/0136045 A1 | 5/2014 | Zhu et al. |
| 2014/0136414 A1 | 5/2014 | Abhyanker |
| 2014/0164126 A1 | 6/2014 | Nicholas et al. |
| 2014/0188999 A1 | 7/2014 | Leonard et al. |
| 2014/0195213 A1 | 7/2014 | Kozloski et al. |
| 2014/0201037 A1 | 7/2014 | Mallawarachchi et al. |
| 2014/0201126 A1 | 7/2014 | Zadeh |
| 2014/0214255 A1 | 7/2014 | Dolgov et al. |
| 2014/0222277 A1 | 8/2014 | Tsimhoni et al. |
| 2014/0222577 A1 | 8/2014 | Abhyanker |
| 2014/0282967 A1 | 9/2014 | Maguire |
| 2014/0297116 A1 | 10/2014 | Anderson et al. |
| 2014/0306833 A1 | 10/2014 | Ricci |
| 2014/0309789 A1 | 10/2014 | Ricci |
| 2014/0309806 A1 | 10/2014 | Ricci |
| 2014/0309864 A1 | 10/2014 | Ricci |
| 2014/0309891 A1 | 10/2014 | Ricci |
| 2014/0310186 A1 | 10/2014 | Ricci |
| 2014/0316671 A1 | 10/2014 | Okamoto |
| 2014/0324268 A1 | 10/2014 | Montemerlo et al. |
| 2014/0330479 A1 | 11/2014 | Dolgov |
| 2014/0358331 A1 | 12/2014 | Prada Gomez et al. |
| 2014/0358353 A1 | 12/2014 | Ibanez-Guzman et al. |
| 2015/0006005 A1 | 1/2015 | Yu et al. |

(56) References Cited

U.S. PATENT DOCUMENTS

| | | |
|---|---|---|
| 2015/0006014 A1 | 1/2015 | Wimmer et al. |
| 2015/0026092 A1 | 1/2015 | Abboud et al. |
| 2015/0035685 A1 | 2/2015 | Strickland et al. |
| 2015/0051778 A1 | 2/2015 | Mueller |
| 2015/0057891 A1 | 2/2015 | Mudalige et al. |
| 2015/0062340 A1 | 3/2015 | Datta et al. |
| 2015/0062469 A1 | 3/2015 | Fleury |
| 2015/0066282 A1 | 3/2015 | Yopp |
| 2015/0066284 A1 | 3/2015 | Yopp |
| 2015/0070178 A1 | 3/2015 | Kline |
| 2015/0088358 A1 | 3/2015 | Yopp |
| 2015/0095190 A1 | 4/2015 | Hammad et al. |
| 2015/0097866 A1 | 4/2015 | Mochizuki |
| 2015/0120331 A1 | 4/2015 | Russo et al. |
| 2015/0134178 A1 | 5/2015 | Minoiu-Enache |
| 2015/0141043 A1 | 5/2015 | Abramson |
| 2015/0149021 A1 | 5/2015 | Duncan et al. |
| 2015/0160019 A1 | 6/2015 | Biswal et al. |
| 2015/0166059 A1 | 6/2015 | Ko |
| 2015/0187019 A1 | 7/2015 | Fernandes |
| 2015/0196256 A1 | 7/2015 | Venkatraman et al. |
| 2015/0210280 A1 | 7/2015 | Agnew et al. |
| 2015/0232065 A1 | 8/2015 | Ricci et al. |
| 2015/0235480 A1 | 8/2015 | Cudak |
| 2015/0242953 A1 | 8/2015 | Suiter |
| 2015/0293994 A1 | 10/2015 | Kelly |
| 2015/0338226 A1 | 11/2015 | Mason et al. |
| 2015/0339639 A1 | 11/2015 | Choe |
| 2016/0001781 A1 | 1/2016 | Fung et al. |
| 2016/0026182 A1 | 1/2016 | Boroditsky et al. |
| 2016/0063761 A1 | 3/2016 | Sisbot et al. |
| 2016/0075512 A1 | 3/2016 | Lert, Jr. |
| 2016/0078695 A1 | 3/2016 | McClintic et al. |
| 2016/0078758 A1 | 3/2016 | Basalamah |
| 2016/0090100 A1 | 3/2016 | Oyama et al. |
| 2016/0139594 A1 | 5/2016 | Okumura et al. |
| 2016/0140507 A1 | 5/2016 | Stevens et al. |
| 2016/0176409 A1 | 6/2016 | Kirsch et al. |
| 2016/0202700 A1 | 7/2016 | Sprigg |
| 2016/0205146 A1 | 7/2016 | Sugioka et al. |
| 2016/0264131 A1 | 9/2016 | Chan et al. |
| 2016/0303969 A1 | 10/2016 | Akula |
| 2016/0304122 A1 | 10/2016 | Herzog et al. |
| 2016/0334797 A1 | 11/2016 | Ross et al. |
| 2016/0344737 A1 | 11/2016 | Anton |
| 2016/0355192 A1 | 12/2016 | James et al. |
| 2016/0358477 A1 | 12/2016 | Ansari |
| 2016/0364823 A1 | 12/2016 | Cao |
| 2017/0001650 A1 | 1/2017 | Park |
| 2017/0010613 A1 | 1/2017 | Fukumoto |
| 2017/0021830 A1 | 1/2017 | Feldman et al. |
| 2017/0021837 A1 | 1/2017 | Ebina |
| 2017/0057542 A1 | 3/2017 | Kim et al. |
| 2017/0106876 A1 | 4/2017 | Gordon et al. |
| 2017/0123428 A1 | 5/2017 | Levinson et al. |
| 2017/0129487 A1 | 5/2017 | Wulf |
| 2017/0137023 A1 | 5/2017 | Anderson et al. |
| 2017/0248949 A1 | 8/2017 | Moran et al. |
| 2018/0075309 A1 | 3/2018 | Sathyanarayana et al. |
| 2018/0093631 A1 | 4/2018 | Lee et al. |

FOREIGN PATENT DOCUMENTS

| | | |
|---|---|---|
| CN | 1376599 A | 10/2002 |
| CN | 201004265 Y | 1/2008 |
| CN | 201635568 U | 11/2010 |
| CN | 202012052 | 10/2011 |
| CN | 202038228 U | 11/2011 |
| CN | 102650882 | 8/2012 |
| CN | 202772924 | 3/2013 |
| CN | 104900018 A | 9/2015 |
| EP | 0582236 | 2/1994 |
| GB | 2498793 A | 7/2013 |
| WO | 2006003661 A2 | 1/2006 |
| WO | 2014058263 | 4/2014 |
| WO | 2014066721 | 5/2014 |
| WO | 2014147361 | 9/2014 |
| WO | 2014148975 | 9/2014 |
| WO | 2014148976 | 9/2014 |
| WO | 2015024616 | 2/2015 |
| WO | 2015056105 | 4/2015 |
| WO | 2015156146 A1 | 10/2015 |

OTHER PUBLICATIONS

Anonymous, "Car Built-In Mechanism to Enforce Mandatory Self-Driving Mode", ip.com, No. 000234916, Feb. 14, 2014, pp. 1-3.

T. Horberry et al., "Driver Distraction: The Effects of Concurrent In-Vehicle Tasks, Road Enviornment Complexity and Age on Driving Performance", Elsevier Ltd., Accident Analysis and Prevention, 38, 2006, pp. 185-191.

J. Miller, "Self-Driving Car Technology's Benefits, Potential Risks, and Solutions", The Energy Collective, theenergycollective.com, Aug. 19, 2014, pp. 1-7.

Chen S, et al., "A Crash Risk Assessment Model for Roas Curves". Inproceedings 20th International Technical Conference on the Enhanced Saftey of Vehicles., 2007. Lyon, France.

J. Wei et al., "Towards a Viable Autonomous Driving Research Platform", IEEE, Intelligent Vehicles Symposium (IV), 2013, pp. 1-8.

Anonymous, "Diagnostics Mechanism for Self-Driving Cars to Validate Self-Driving Capabilities", ip.com, Jun. 6, 2014, pp. 1-5. ip.com.

Brownell, "Shared Autonomous Taxi Networks: An Analysis of Transportation Demand in NJ and a 21st Century Solution for Congestion", Dissertation, Princeton University, 2013, pp. 1-122.

Sessa et al., "Blueprint of Alternative City Cyber-Mobility Take-U Scenarios", Seventh Framework Programme Theme SST.2012.3.1-4, Automated Urban Vehicles Collaborative Project—Grant Agreement No. 314190, 2013, pp. 1-63.

Lutin et al., "The Revolutionary Development of Self-Driving Vehicles and Implications for the Transportation Engineering Profession", ITE Journal 83.7, 2013, pp. 28-32.

A. Hars, "Self-Driving Cars: The Digital Transformation of Mobility", Marktplatze Im Umbruch, Springer Berlin Heidelberg, 2015, pp. 539-549.

Jimenez et al.; "Autonomous collision avoidance system based on accurate knowledge of the vehicle surroundings"; Inst Engineering Technology-IET; IET Intelligent Transport Systems vol. 9, No. 1, pp. 105-117; 2015; England.

Anonymous, "Avoiding Crashes With Self-Driving Cars: Today's Crash-Avoidance Systems are the Mile Markers to Tomorrows Autonomous Vehicles". Consumer Reports Magazine, Feb. 2014. Web. Sep. 22, 2016. <http://www.consumerreports.org/cro/magazine/2014/04/the-road-to-self-driving-cars/index.htm>.

Anonymous, "Google Files Patent for Second-Gen Autonomous Vehicle Without a Steering Wheel, Brake Pedal & More". patentlymobile.com, Nov. 27, 2015. Web. Sep. 22, 2016. <http://www.patentlymobile.com/2015/11/google-files-patent-for-second-gen-autonomous-vehicle-without-a-steering-wheel-brake-pedal-more.html>.

C. Berger et al., "Cots-Architecture With a Real-Time OS for a Self-Driving Miniature Vehicle", SAFECOMP 2013—Workshop ASCOMS of the 32nd International Conference on Computer Safety, Reliability and Security, Sep. 2013, Toulouse, France, pp. 1-13.

P. Mell et al., "Nist Definition Fo Cloud Computing", National Institute of Standards and Tchnology, Information Technology Labratory, Sep. 2011, pp. 1-7.

U.S. Appl. No. 14/833,652 Non-Final Office Action dated Apr. 24, 2017.

List of IBM Patents or Patent Applications Treated as Related. Oct. 26, 2017.

AUTOMATED SPATIAL SEPARATION OF SELF-DRIVING VEHICLES FROM OTHER VEHICLES BASED ON OCCUPANT PREFERENCES

BACKGROUND

The present disclosure relates to the field of vehicles, and specifically to the field of self-driving vehicles. Still more specifically, the present disclosure relates to the field of automatically providing spatial separation between self-driving vehicles and other vehicles.

Self-driving vehicles (SDVs) are vehicles that are able to autonomously drive themselves through private and/or public spaces. Using a system of sensors that detect the location and/or surroundings of the SDV, logic within or associated with the SDV controls the propulsion, stopping, and steering of the SDV based on the sensor-detected location and surroundings of the SDV.

SUMMARY

A computer-implemented method, system, and/or computer program product automatically provides spatial separation between a self-driving vehicle (SDV) operating in an autonomous mode and another vehicle on a roadway. One or more processors receive an emotional state descriptor for at least one occupant of the SDV and determine an emotional state of the occupant(s) of the SDV. A vehicle detector on the SDV detects another vehicle and the size of the other vehicle within a predefined proximity of the SDV. A control mechanisms controller determines that a field of view for the occupants in the SDV is blocked by the size of the other vehicle. The processor(s) issue spatial separation instructions to the control mechanisms controller on the SDV to adjust a spacing between the SDV and the other vehicle based on the emotional state descriptor for the occupant(s) in the SDV and the field of view for the occupant(s) in the SDV that is blocked by the size of the other vehicle.

DETAILED DESCRIPTION

Figure 1:
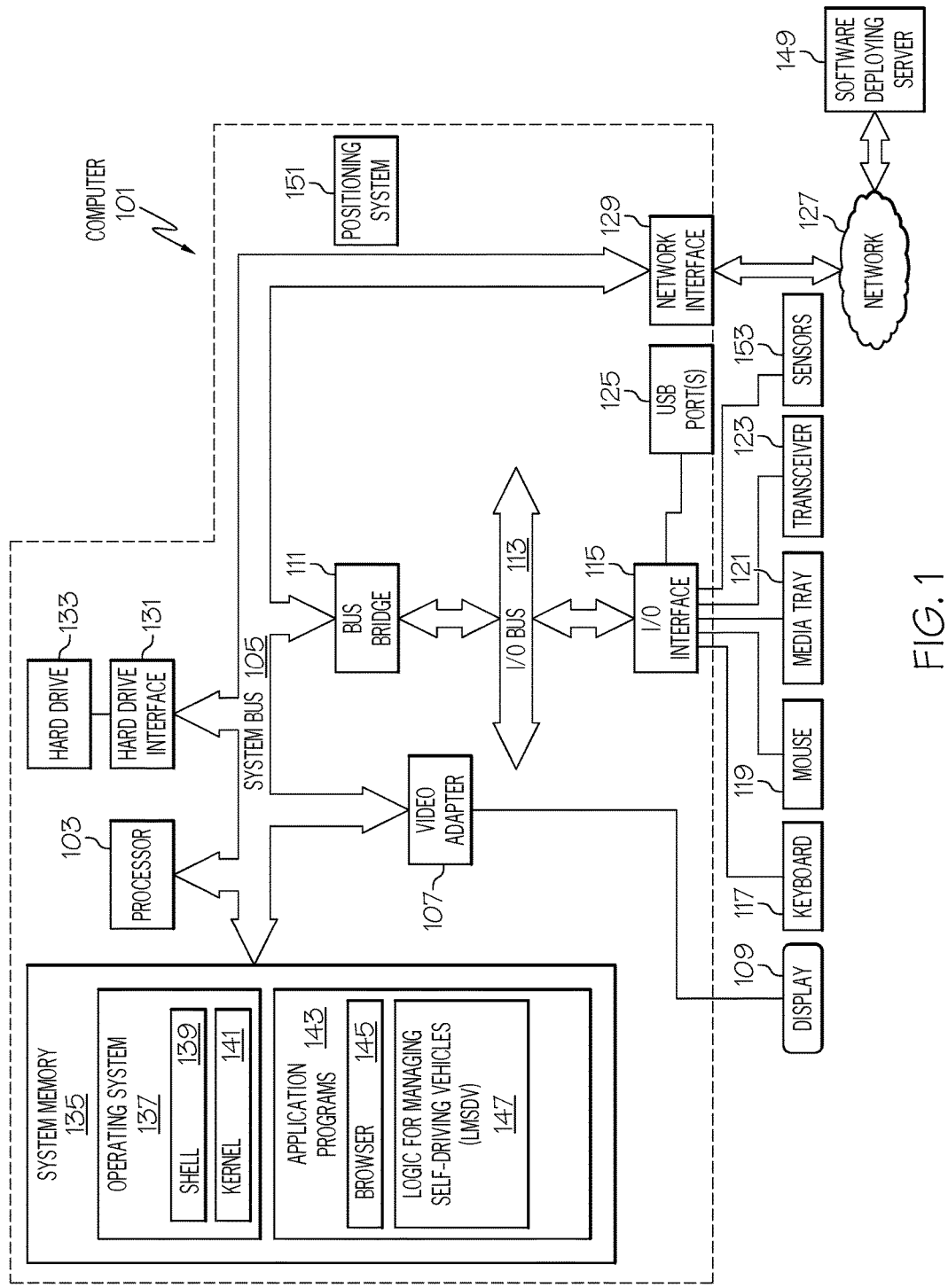
FIG. 1 depicts an exemplary system and network in which the present disclosure may be implemented.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The present invention provides a new technological solution to setting a desired distance between a self-driving vehicle (SDV) and another vehicle based on emotional factors and/or cognitive factors ascribed to occupants of the SDV. The other vehicle may be another SDV operating in autonomous (self-driving) mode, an SDV that is currently being controlled by a human driver (manual mode), or a non-SDV vehicle that is always controlled by a human driver.

Emotional factors include, but are not limited to, psychological emotions such as fear, calm, anger, anxiety, etc.

Cognitive factors include, but are not limited to, a person's mental abilities to understand and interpret circumstantial situations, such as the capabilities of autonomous controllers in an SDV.

Thus, if a person is uncomfortable with a spacing between the SDV in which he/she is riding and another vehicle, whether for issues caused by irrational emotional factors or rational cognitive factors, then the distance between the SDV and the other vehicle is adjusted until the person is comfortable (as indicated by feedback from the person). This feedback may be textual (e.g., as an input to a display) and/or biometric (e.g., as biometric indicators from biometric sensors), in accordance with various embodiments of the present invention.

In an embodiment of the present invention, the spatial distance between the SDV and the other vehicle is further adjusted according to the vehicle size/type of the other vehicle. For example, an SDV may be following a tall truck. Following closely to the tall truck results in the field of view of occupants of the SDV being blocked, thus leading to a feeling of being closed in, if not a feeling of being physically in danger.

In an embodiment of the present invention, the emotional state of the occupants is detected by biometrics of the occupants. Such biometrics, which are captured by an onboard video camera, wearable biometric sensors, etc., are used to automatically adjust the minimum distance between the SDV and the other vehicle in order to create a riding environment that is comfortable and not fear-inducing.

In an embodiment of the present invention, the emotional state of one or more of the occupants of the SDV is received by an input device (e.g., a touch screen), which allows the occupant(s) to adjust a dial, knob, slider, or similar graphical interface device to set emotional states used to establish a minimum distance between the SDV and the other vehicle. Based on these settings (from the input device or from sensors), the SDV maintains and/or communicates its minimum distance requirements to surrounding vehicles.

In an embodiment of the present invention, processors perform an emotional state assessment of the SDV's occupants by analyzing video and/or biometric sensor outputs, in order to determine the comfort level and/or the discomfort level of the SDV's occupants due to surrounding vehicles. In one embodiment, a further adjustment is made to minimum distance settings based on this assessment.

In an embodiment of the present invention, a driver profile provides an indication of an SDV occupant's abilities and preferences, including the SDV occupant's (base) emotional state.

In an embodiment of the present invention, the spacing between the SDV and the other vehicle is further adjusted according to other occupants (adults, children, pets) of the SDV, which may be assumed to alter the emotional state of the driver of the SDV (i.e., the person who takes control of the SDV when the SDV switches from "autonomous mode" to "manual mode").

In an embodiment of the present invention, occupant profiles are downloaded from smart phones or wearable devices of the occupants. The occupant profiles may indicate a preferred distance (spatial or temporal) between another vehicle and the front, side, or rear of the SDV. However, in a preferred embodiment, the occupant profile indicates an overall emotional trait of the occupant (i.e., one who is a risk taker, one who has trust in technology, one who is mistrustful of new technology, one who is uncomfortable in confined areas, etc.). This overall emotional trait may be derived from a questionnaire, a history of biometric readings, etc. Based on this overall emotion trait, the system adjusts spacing between an SDV in which the occupant is riding and other vehicles, as described herein.

With reference now to the figures, and in particular to FIG. 1, there is depicted a block diagram of an exemplary system and network that may be utilized by and/or in the implementation of the present invention. Some or all of the exemplary architecture, including both depicted hardware and software, shown for and within computer 101 may be utilized by software deploying server 149 shown in FIG. 1, and/or coordinating server 201 depicted in FIG. 2, and/or self-driving vehicle (SDV) on-board computer 301 shown in FIG. 3, and/or coordinating server 401 depicted in FIG. 4.

Exemplary computer 101 includes a processor 103 that is coupled to a system bus 105. Processor 103 may utilize one or more processors, each of which has one or more processor cores. A video adapter 107, which drives/supports a display 109, is also coupled to system bus 105. System bus 105 is coupled via a bus bridge 111 to an input/output (I/O) bus 113. An I/O interface 115 is coupled to I/O bus 113. I/O interface 115 affords communication with various I/O devices, including a keyboard 117, a mouse 119, a media tray 121 (which may include storage devices such as CD-ROM drives, multi-media interfaces, etc.), a transceiver 123 (capable of transmitting and/or receiving electronic communication signals), and external USB port(s) 125. While the format of the ports connected to I/O interface 115 may be any known to those skilled in the art of computer architecture, in one embodiment some or all of these ports are universal serial bus (USB) ports.

Figure 2:
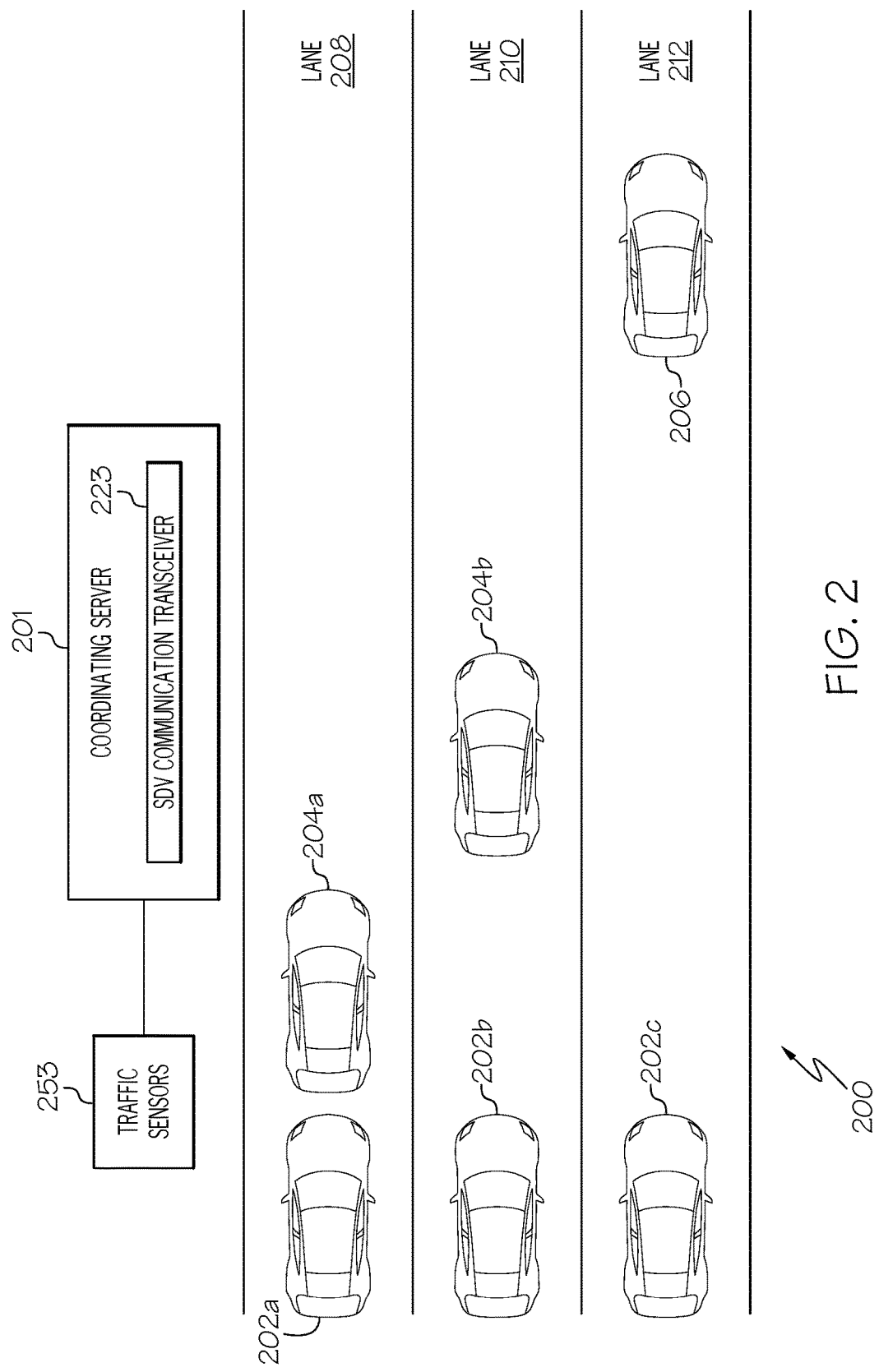
FIG. 2 illustrates exemplary self-driving vehicles (SDVs) operating on a roadway.

As depicted, computer 101 is able to communicate with a software deploying server 149 and/or other devices/systems (e.g., coordinating server 201, one or more of the SDVs 202a-202c, and/or one or more of SDVs 204a-204b shown in FIG. 2) using a network interface 129. Network interface 129 is a hardware network interface, such as a network interface card (NIC), etc. Network 127 may be an external network such as the Internet, or an internal network such as an Ethernet or a virtual private network (VPN). In one or more embodiments, network 127 is a wireless network, such as a Wi-Fi network, a cellular network, etc.

A hard drive interface 131 is also coupled to system bus 105. Hard drive interface 131 interfaces with a hard drive 133. In one embodiment, hard drive 133 populates a system memory 135, which is also coupled to system bus 105. System memory is defined as a lowest level of volatile memory in computer 101. This volatile memory includes additional higher levels of volatile memory (not shown), including, but not limited to, cache memory, registers and buffers. Data that populates system memory 135 includes computer 101's operating system (OS) 137 and application programs 143.

OS 137 includes a shell 139, for providing transparent user access to resources such as application programs 143. Generally, shell 139 is a program that provides an interpreter and an interface between the user and the operating system. More specifically, shell 139 executes commands that are entered into a command line user interface or from a file. Thus, shell 139, also called a command processor, is generally the highest level of the operating system software hierarchy and serves as a command interpreter. The shell provides a system prompt, interprets commands entered by keyboard, mouse, or other user input media, and sends the interpreted command(s) to the appropriate lower levels of the operating system (e.g., a kernel 141) for processing. While shell 139 is a text-based, line-oriented user interface, the present invention will equally well support other user interface modes, such as graphical, voice, gestural, etc.

As depicted, OS 137 also includes kernel 141, which includes lower levels of functionality for OS 137, including providing essential services required by other parts of OS 137 and application programs 143, including memory management, process and task management, disk management, and mouse and keyboard management.

Application programs 143 include a renderer, shown in exemplary manner as a browser 145. Browser 145 includes program modules and instructions enabling a world wide web (WWW) client (i.e., computer 101) to send and receive network messages to the Internet using hypertext transfer protocol (HTTP) messaging, thus enabling communication with software deploying server 149 and other systems.

Application programs 143 in computer 101's system memory (as well as software deploying server 149's system memory) also include Logic for Managing Self-Driving Vehicles (LMSDV) 147. LMSDV 147 includes code for implementing the processes described below, including those described in FIGS. 2-5. In one embodiment, computer 101 is able to download LMSDV 147 from software deploying server 149, including in an on-demand basis, wherein the code in LMSDV 147 is not downloaded until needed for execution. In one embodiment of the present invention, software deploying server 149 performs all of the functions associated with the present invention (including execution of LMSDV 147), thus freeing computer 101 from having to use its own internal computing resources to execute LMSDV 147.

Also within computer 101 is a positioning system 151, which determines a real-time current location of computer 101 (particularly when part of a self-driving vehicle as described herein). Positioning system 151 may be a combination of accelerometers, speedometers, etc., or it may be a global positioning system (GPS) that utilizes space-based satellites to provide triangulated signals used to determine two or three dimensional locations.

Also associated with computer 101 are sensors 153, which detect an environment of the computer 101. More specifically, sensors 153 are able to detect other vehicles, road obstructions, pedestrians, construction sites, etc. For example, if computer 101 is on board a self-driving vehicle (SDV), then sensors 153 may be cameras, radar transceivers, microphones, etc. that allow the SDV to detect the environment (e.g., other vehicles, road obstructions, pedestrians, etc.) of that SDV. Similarly, if hardware within computer 101 is used by coordinating server 201 shown in FIG. 2, then sensors 153 may be cameras, radar transceivers, radio frequency identifier (RFID) transceivers, etc. that allow the coordinating server 201 to identify oncoming and/or passing-by vehicles, including SDVs.

The hardware elements depicted in computer 101 are not intended to be exhaustive, but rather are representative to highlight essential components required by the present invention. For instance, computer 101 may include alternate memory storage devices such as magnetic cassettes, digital versatile disks (DVDs), Bernoulli cartridges, and the like. These and other variations are intended to be within the spirit and scope of the present invention.

With reference now to FIG. 2, exemplary self-driving vehicles (SDVs) 202a-202c (where "c" is an integer) and SDVs 204a-204b (where "b" is also an integer) traveling along a roadway 200 in accordance with one or more embodiments of the present invention is presented. For purposes of illustration, assume that all of the SDVs 202a-202c are being operated in a self-driving (i.e., autonomous) mode, while SDVs 204a-204b may or may not be operating in autonomous mode. That is, while vehicles 204a-204b have hardware required to enable vehicles 204a-204b to operate in self-driving (autonomous) mode, vehicles 204a-204b may be operating in manual mode, in which they are controlled by manual inputs that are provided by a human driver. Furthermore, assume that vehicle 206 shown in FIG. 2 is not equipped with SDV-enabling hardware, such that vehicle 206 is always operated by a human driver.

Figure 3:
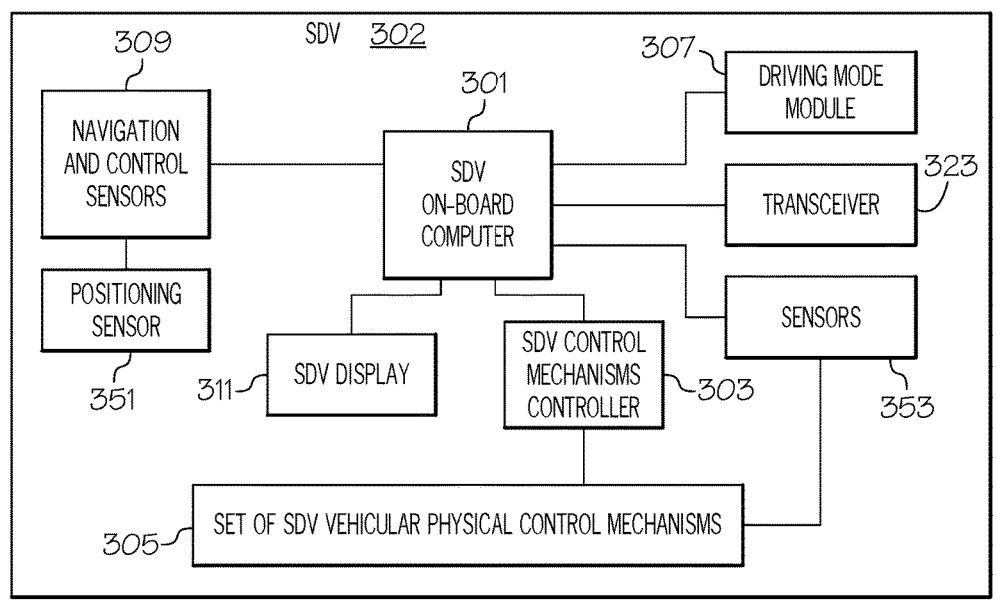
FIG. 3 depicts additional detail of control hardware within an SDV.

Additional detail of one or more embodiments of one or more of the SDVs 202a-202c and/or SDVs 204a-204b shown in FIG. 2 is presented in FIG. 3 as SDV 302. As shown in FIG. 3, SDV 302 has an SDV on-board computer 301 that controls operations of the SDV 302. According to directives from a driving mode module 307, SDV 302 can be selectively operated in manual mode or autonomous mode.

While in manual mode, SDV 302 operates as a traditional motor vehicle, in which a human driver controls the engine, steering mechanism, braking system, horn, signals, etc. found on a motor vehicle. These vehicle mechanisms may be operated in a "drive-by-wire" manner, in which inputs to an SDV control mechanisms controller 303 by the driver result in output signals that control the SDV vehicular physical control mechanisms 305 (e.g., the engine throttle, steering mechanisms, braking systems, turn signals, etc.).

While in autonomous mode, SDV 302 operates without the input of a human driver, such that the engine, steering mechanism, braking system, horn, signals, etc. are still controlled by the SDV control mechanisms controller 303, but now are under the control of the SDV on-board computer 301. That is, by processing inputs taken from navigation and control sensors 309 (which may use inputs from a positioning sensor 351, analogous to positioning sensor 151 shown in FIG. 1, to indicate the current position of the SDV 302) and the driving mode module 307 indicating that the SDV 302 is to be controlled autonomously, then driver inputs are no longer needed.

As just mentioned, the SDV on-board computer 301 uses outputs from navigation and control sensors 309 to control the SDV 302. Navigation and control sensors 309 include hardware sensors that (1) determine the location of the SDV 302; (2) sense other cars and/or obstacles and/or physical structures around SDV 302; (3) measure the speed and direction of the SDV 302; and (4) provide any other inputs needed to safely control the movement of the SDV 302.

With respect to the feature of (1) determining the location of the SDV 302, this can be achieved through the use of a positioning system such as positioning system 151 shown in FIG. 1. Positioning system 151 may use a global positioning system (GPS), which uses space-based satellites that provide positioning signals that are triangulated by a GPS receiver to determine a 3-D geophysical position of the SDV 302. Positioning system 151 may also use, either alone or in conjunction with a GPS system, physical movement sensors such as accelerometers (which measure rates of changes to a vehicle in any direction), speedometers (which measure the instantaneous speed of a vehicle), air-flow meters (which measure the flow of air around a vehicle), etc. Such physical movement sensors may incorporate the use of semiconductor strain gauges, electromechanical gauges that take readings from drivetrain rotations, barometric sensors, etc.

With respect to the feature of (2) sensing other cars and/or obstacles and/or physical structures around SDV 302, the positioning system 151 may use radar or other electromagnetic energy that is emitted from an electromagnetic radiation transmitter (e.g., transceiver 323 shown in FIG. 3), bounced off a physical structure (e.g., another car), and then received by an electromagnetic radiation receiver (e.g., transceiver 323). By measuring the time it takes to receive back the emitted electromagnetic radiation, and/or evaluating a Doppler shift (i.e., a change in frequency to the electromagnetic radiation that is caused by the relative movement of the SDV 302 to objects being interrogated by the electromagnetic radiation) in the received electromagnetic radiation from when it was transmitted, the presence and location of other physical objects can be ascertained by the SDV on-board computer 301.

With respect to the feature of (3) measuring the speed and direction of the SDV 302, this can be accomplished by taking readings from an on-board speedometer (not depicted) on the SDV 302 and/or detecting movements to the steering mechanism (also not depicted) on the SDV 302 and/or the positioning system 151 discussed above.

With respect to the feature of (4) providing any other inputs needed to safely control the movement of the SDV 302, such inputs include, but are not limited to, control signals to activate a horn, turning indicators, flashing emergency lights, etc. on the SDV 302.

Returning now to FIG. 2, assume that roadway 200 has multiple lanes, including lane 208, lane 210, and lane 212.

As shown in lane 208, SDV 202a is traveling very close to SDV 204a (e.g., within a predetermined distance that has been deemed safe for two SDV's moving at a certain speed under certain road conditions according to the parameters of the SDVs). That is, for current road conditions on lane 208 (e.g., traffic volume, weather, potholes, etc. on lane 208), as well as the state of SDV 202a and SDV 204a (e.g., the condition of their tires, their brakes, their autonomous control system's, etc.), the distance between SDV 202a and/or SDV 204a may be safe.

In one embodiment of the present invention, the safe distance between two SDVs is based on the abilities of the SDV. For example, SDV 202a and/or SDV 204a shown in FIG. 2 may have certain types of tires (e.g., rain tires), velocity ability (e.g., ability to travel in excess of 70 miles per hour), and braking abilities (e.g., four wheel disk brakes) that allow them to safely travel at 70 miles per hour within 10 feet of one another. However, if SDV 202a and/or SDV 204a do not meet these standards, then the minimum distance between them will be adjusted accordingly (e.g., to travel within 200 feet of one another at 70 miles per hour).

In one embodiment of the present invention, determining the type and/or condition of tires on SDVs is performed by image analysis. For example, assume that the sensors 353 shown in FIG. 3 on SDV 302 are on-board cameras aimed at the tires on SDV 302. The nature of the tread, inflation, etc. of the tires is determined by image analysis of images of the tires captured by these cameras, thereby determining one of the factors that determine the condition of the SDV 302.

In one embodiment of the present invention, adjusting the spatial separation between an SDV and another vehicle is based on other dangerous conditions of the SDV and/or the other vehicle. For example, assume that SDV 202a is following SDV 204a closely, as shown in lane 208 in FIG. 2, or that SDV 202c is following non-SDV vehicle 206 in lane 212. Assume further that there is a visible danger that is posed to SDV 202a by SDV 204a (or to SDV 202c by vehicle 206). This visible danger may be visually observed by occupants of SDV 202a/202c and/or by sensors (e.g., sensors 353 shown in FIG. 3) on the SDV 202a/202c.

For example, assume that SDV 204a has a loose load (e.g., a mattress) tied to its top, which is showing indications of flying off at any moment (e.g., the straps holding the mattress are loose, etc.). Similarly, SDV 204a may have a wobbling tire that appears to be degrading the stability of SDV 204a, or SDV 204a may be swerving back and forth within lane 208. Similarly, SDV 204a may be a tow truck that is towing another vehicle (not shown), which is showing signs of potentially becoming unattached to the tow truck (SDV 204a).

As a result of such visible dangers, two results may occur.

First, occupants within SDV 202a may become emotionally concerned (anxious, fearful, etc.) just by the sight of the visible danger. As such, sensors 353 on the SDV on-board computer 301 will detect the visible danger, and will adjust the spatial separation (e.g., by backing away or moving to another lane) from the SDV 204a, simply to alleviate and/or avoid the expected increase in discomfort that would be experienced by the occupants of SDV 202a.

Second, occupants within SDV 202a may be physically injured if the visible danger comes to fruition (e.g., the mattress flies off the top of SDV 204a). Again, sensors 353 on the SDV on-board computer 301 will detect the visible danger, and will adjust the spatial separation (e.g., by backing away or moving to another lane) from the SDV 204a, in order to protect the physical safety of the occupants of SDV 202a.

In one embodiment of the present invention, a risk analysis is performed on the visible danger. That is, a record of accidents that have occurred due to the same type of danger as the type being observed is retrieved. For example, this record of accidents is for all accidents in which a loose mattress flies off the top of a vehicle. If the record of such accidents indicates that more than a predefined percentage (e.g., 95%) of such accidents occurred when the trailing vehicle (e.g., SDV 202a) was within 200 feet of the lead vehicle (e.g., SDV 204a with the loose mattress on top), then the SDV on-board computer 301 on SDV 202a will cause SDV 202a to automatically drop back more than 200 feet behind SDV 204a and/or to automatically move to another lane.

In one or more embodiments of the present invention, the amount of discomfort or physical threat that occupants of the SDV may experience is speed dependent. For example, if SDV 202a and SDV 204a are both traveling at 20 miles per hour, then a spatial separation of only 50 feet between SDV 202a and SDV 204a may be comfortable/safe for the occupants of the SDV 202a and/or the SDV 204a. However, if SDV 202a and SDV 204a are both traveling at 70 miles per hour, then a spatial separation of only 50 feet may be uncomfortable and/or unsafe for the occupants of SDV 202a and/or SDV 204a. Thus, the SDV on-board computer 301 within the SDV 202a and/or SDV 204a will automatically adjust the spatial separation between SDV 202a and SDV 204a (e.g., expand the spatial separation to 300 feet) based on SDV 202a and SDV 204a traveling at 70 miles per hour.

In accordance with one or more embodiments and as described herein, the amount of discomfort of occupants of an SDV (which leads to an adjustment of spatial separation between the SDV and another vehicle) may be for occupants of a trailing vehicle (e.g., SDV 202a shown in FIG. 2) or a leading vehicle (e.g., SDV 204a shown in FIG. 2). Thus, based on the discomfort of occupants/passengers of either SDV, the presently-described invention will adjust the spatial separation between the two vehicles.

In one embodiment of the present invention, the adjustment to the spatial separation is created by the SDV on-board computer 301 in the SDV holding the uncomfortable occupants. That is, if the occupants of SDV 202a are uncomfortable with the amount of spatial separation between SDV 202a and SDV 204a, then the SDV on-board computer 301 in SDV 202a will adjust this spatial separation. Similarly, if the occupants of SDV 204a are uncomfortable with the amount of spatial separation between SDV 202a and SDV 204a, then the SDV on-board computer 301 in SDV 204a will adjust this spatial separation. However, in another embodiment, one vehicle will issues instructions to another SDV to adjust the spatial separation.

For example, assume that SDV 204a cannot speed up, due to a posted speed limit, heavy traffic, upcoming traffic congestion, upcoming construction zones, etc. As such, SDV 204a will issue a request (or an instruction) to SDV 202a to slow down, thereby increasing the spatial separation between SDV 202a and SDV 204a.

Similarly, the occupants of non-SDV vehicle 206 may be uncomfortable with the limited spatial separation between SDV 202c and vehicle 206, and yet are unable to speed up for reasons just mentioned (e.g., heavy traffic, upcoming traffic congestion, upcoming construction zones, etc.). Although vehicle 206 is not equipped with an SDV on-board computer 301, it may still be equipped with a special transmitter, which sends requests/instructions to proximate SDVs (e.g., SDV 202c) to adjust their spatial separation from vehicle 206.

In one embodiment of the present invention, the trailing vehicle (e.g., SDV 202a shown in FIG. 2) may be carrying fragile cargo. This fragile cargo may be inanimate (e.g., fragile glass) or live (e.g., a pet, a child, etc.). The operator of SDV 202a may be concerned that any sudden stopping or braking of SDV 202a may cause the fragile cargo to fall over or otherwise move within the cabin of the SDV 202a in an unsafe manner. As such, the operator of the SDV 202a may direct the SDV on-board computer 301 within the SDV 202a to slow the SDV 202a down, thus providing additional spatial separation between SDV 202a and SDV 204a (or any other SDV and/or non-SDV vehicle).

Continuing with the discussion of FIG. 2, the depicted "tailgating" in lane 208 may be perfectly comfortable for some types of occupants of SDV 202a and/or SDV 204a (e.g., occupants who have a high trust in technology, or are simply used to traveling in close proximity to other vehicles), but may cause discomfort to other type of occupants of SDV 202a and/or SDV 204. As such, the spacing around the SDV 202a is adjusted accordingly.

For example, assume that occupants of SDV 202a are comfortable tailgating another SDV 204a. If so, then the minimal spacing shown in lane 208 between SDV 202a and SDV 204a is acceptable to the occupants of SDV 202a and/or SDV 204a.

However, assume now that the occupants of SDV 202b are not comfortable tailgating another SDV 204b. In this case, the SDV on-board computer 301 shown in FIG. 3 will cause SDV 202b to slow down, thus providing the additional spacing between SDV 202b and SDV 204b, as shown in lane 210.

In one embodiment of the present invention, a descriptor of whether SDV 204b is operating in autonomous mode or manual mode is sent to the SDV on-board computer 301 within SDV 202b. If SDV 204b is currently operating in manual mode, or if SDV 202c is following a non-SDV vehicle 206, then the occupants of SDV 202*b* and/or SDV 202*c* may be less comfortable respectively following SDV 204*b* and/or vehicle 206. As such, additional spacing is afforded between SDV 202*c* and vehicle 206, as shown in lane 212.

In an embodiment of the present invention, an SDV display 311 (see FIG. 3) within the cabin of the SDV 302 alerts the occupant of SDV 202*b*/202*c* that he/she is following a non-SDV vehicle (204*b*/206). This alert thus causes the occupant of SDV 202*b*/202*c* to feel differently about tailgating the other (204*b*/206) than if the other vehicle were operating in autonomous SDV mode.

If sensors within SDV 202*a* indicate the presence of small children, pets, other occupants (e.g., using sensors 353 shown in FIG. 3 that pick up sounds, pressure on seats, etc.) within the cabin of vehicle 202*a*, which are likely distractions to the driver of the vehicle 202*a*, then the coordinating server 201 and/or the SDV on-board computer 301 within SDV 202*a* may determine that one or more occupants of SDV 202*a* are likely distracting one another, such that the occupants do not notice other vehicles on lane 208, and thus let SDV 202*a* continue to tailgate SDV 204*a*. Alternatively, coordinating server 201 and/or the SDV on-board computer 301 within SDV 202*a* may interpret the presence of other occupants as being anxiety producing (e.g., as indicated by angry voices, nervous looks, etc.), and thus will automatically cause the SDV 202*a* to increase the distance between SDV 202*a* and SDV 204*a*, thereby removing one further source of stress to the occupant(s) of SDV 202*a*.

Note that this distance between SDV 202*a* and SDV 204*a* may be controlled by either SDV 202*a* or SDV 204*a*. That is, SDV 202*a* may slow down, thus providing more space between SDV 202*a* and SDV 204*a*, and meeting the emotional requirements of the occupants of SDV 202*a*. Alternatively, SDV 204*a* may speed up (i.e., up to a safe and/or legal speed limit), thus providing more space between SDV 202*a* and SDV 204*a* and meeting the emotional requirements of the occupants of SDV 204*a*. In either embodiment (SDV 202*a* slowing down or SDV 204*a* speeding up), once the desired spatial separation is achieved, the speed of the SDV 202*a* or the SDV 204*a* is then readjusted, such that the desired spatial separation between the SDV 202*a* and the SDV 204*a* is maintained.

In one embodiment of the present invention, lane 208 shown in FIG. 2 is limited to SDVs 202*a*/204*a* that are in full autonomous control mode. As such, the spacing of SDVs 202*a*/204*a* to one another is able to be very close since they are (1) able to communicate their operational parameters to one another and/or (2) have much faster response times than human drivers. This allows lane 208 to handle much more overall traffic than lane 210 or lane 212, since the SDVs 202*a*/204*a* are more tightly spaced (compacted), thereby improving the overall laminar flow-rate of vehicles on lane 208. Thus, in one embodiment of the present invention, assume that lane 208 is restricted to SDVs that are closely spaced as shown for SDV 202*a* and SDV 204*a*. As such, only SDVs that are spaced without regard to emotional concerns of the occupants (as described herein) are allowed on lane 208, such that these SDVs travel in a smoother and faster laminar flow. However, if such tight spacing is too uncomfortable for occupants of the SDVs, then these SDVs are required to travel in lane 210 or lane 212, where travel is less efficient due to the greater spacing between vehicles.

While the spacing between SDVs shown in FIG. 2 has been described thus far as being related to the amount of distance between two vehicles in a single lane (i.e., the spacing in front of and/or behind an SDV), in an embodiment such spacing is lateral (i.e., the spacing between two vehicles traveling on adjacent lanes). For example, the occupants of SDV 202*a* may be uncomfortable traveling next to SDV 202*b*, as shown in FIG. 2. As such, SDV 202*a* may speed up and/or slow down until it is no longer next to SDV 202*b*.

Figure 4:
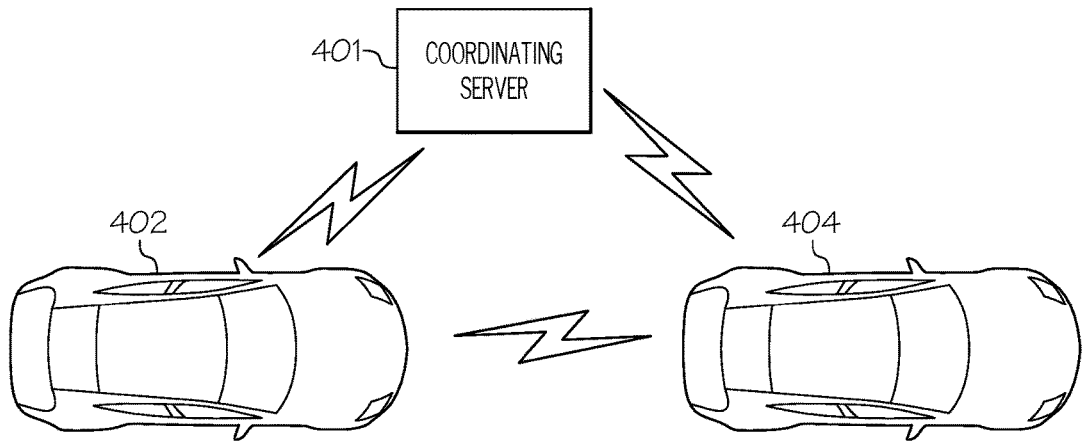
FIG. 4 illustrates exemplary communication linkages among multiple vehicles capable of operating in an autonomous mode and a coordinating server.

With reference now to FIG. 4, communication linkages between the coordinating server 401 (analogous to coordinating server 201 shown in FIG. 2) and/or the SDV 402 (analogous to one or more of the SDVs 202*a*-202*c* shown in FIG. 2) and/or a vehicle 404 (analogous to one or more of the vehicles 204*a*-204*b* shown in FIG. 2) are presented. That is, in one or more embodiments of the present invention, coordinating server 401 is able to communicate with SDV 402 and/or vehicle 404, and SDV 402 is able to directly communicate with vehicle 404, thus allowing SDV 402 to directly control the movement of vehicle 404 (and vice versa) when required.

Figure 5:
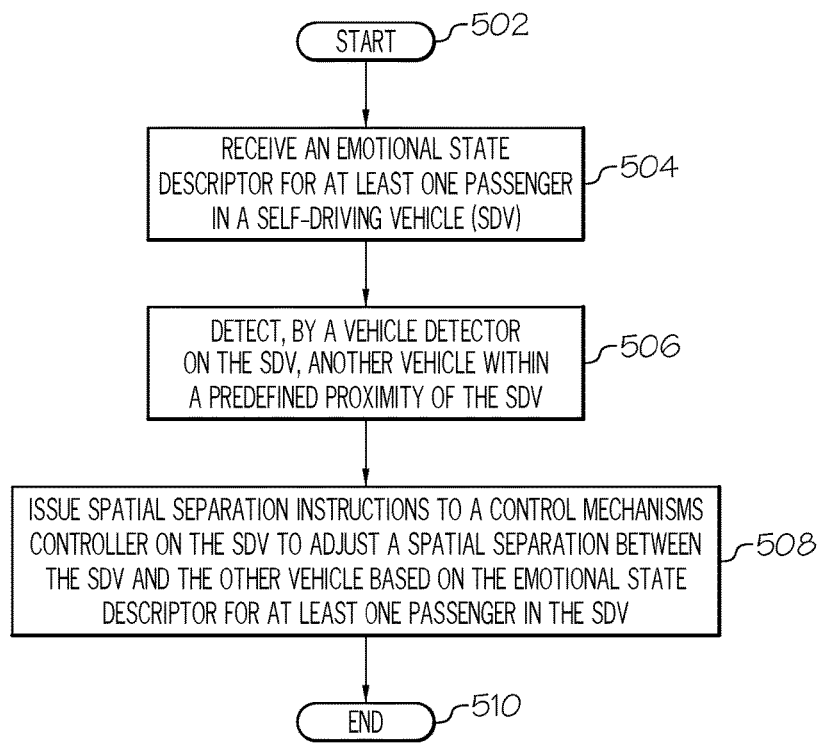
FIG. 5 is a high-level flow chart of one or more steps performed by one or more processors and/or other hardware to automatically provide spatial separation between a self-driving vehicle (SDV) operating in an autonomous mode and another vehicle on a roadway based on an emotional state of at least one occupant of the SDV.

With reference now to FIG. 5, a high-level flow chart of one or more steps performed by one or more processors and/or other hardware to automatically provide spatial separation between a self-driving vehicle (SDV) operating in an autonomous mode and another vehicle on a roadway based on an emotional state of at least one occupant of the SDV is presented.

After initiator block 502, one or more processors receive an emotional state descriptor for at least one occupant of a self-driving vehicle (SDV), as described in block 504.

Figure 6:
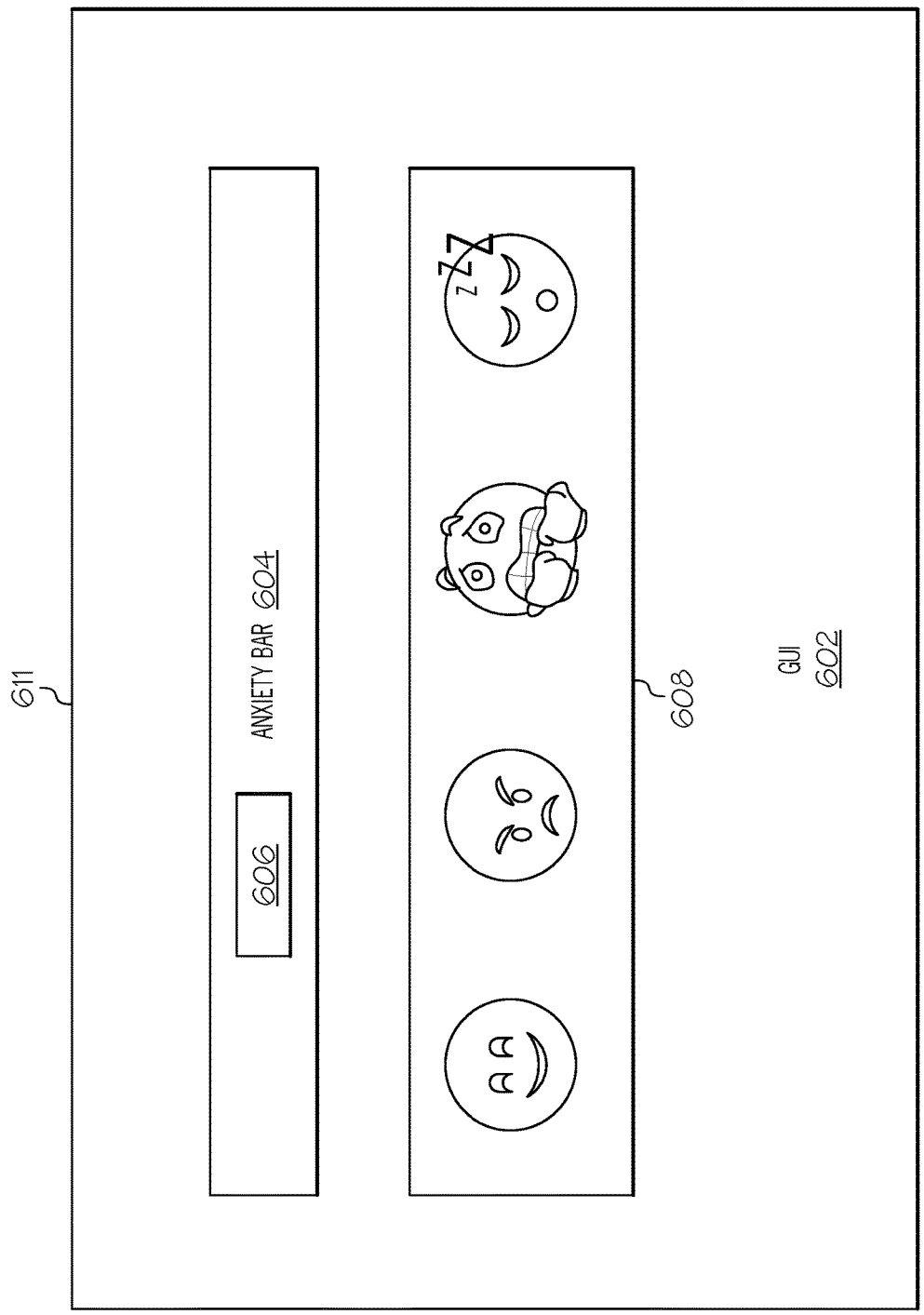
FIG. 6 depicts an exemplary graphical user interface (GUI) that allows an occupant of an SDV to indicate his/her current emotional state.

In one embodiment of the present invention, the emotional state descriptor for the occupant(s) is received from an input device, which receives the emotional state descriptor from the occupant(s). For example, the SDV display 311 within the SDV 302 shown in FIG. 3 may present slider bars, input fields, touch-screen icons, etc. that represent various emotions and their levels in a graphical user interface (GUI), such as GUI 602 depicted in FIG. 6.

GUI 602, which is presented on a display 611 (analogous to SDV display 311 shown in FIG. 3) within a cabin of an SDV (e.g., SDV 302 shown in FIG. 3), allows an occupant of the SDV to input his/her current emotional state.

For example, the occupant of the SDV may slide a slider box 606 along an anxiety bar 604, such that sliding the slider box 606 farther to the right indicates a higher level of anxiety being subjectively experienced by the occupant of the SDV in real time.

Similarly, the occupant of the SDV may click one of the icons shown in feelings box 608 to indicate that he/she is currently feeling happy, angry, nervous, sleepy (as represented by the depicted icons), etc.

Other inputs that can be generated by the occupant include typing text descriptors of his/her subjective emotional state (e.g., happy, angry, nervous, sleepy, etc.) onto the GUI 602 in a data entry box (not shown).

In another embodiment of the present invention, the emotional state descriptor for said occupant of the SDV is not subjectively determined by the occupant (and then entered onto GUI 602 shown in FIG. 6), but rather is determined by a biometric sensor. In one embodiment, this biometric sensor is one of the sensors 353 coupled to the SDV on-board computer 301 shown in FIG. 3. In another embodiment, the biometric sensor is a component of a smart phone or other device carried by an occupant of the SDV. In either embodiment, the biometric sensor is able to detect and output readings indicative of blood pressure, respiratory rate, pupil dilation, skin flushing, galvanic skin resistance from sweating, electrocardiogram reading, etc. Thus, it is the biometric sensor, and not just the subjective feelings of the occupant, that detects the emotional state of the occupant.

Returning now to FIG. 5, a vehicle detector on the SDV detects another vehicle within a predefined proximity of the SDV, as described in block 506. This vehicle detector (e.g., one or more of the sensors 353 shown in FIG. 3) may be a camera, a radar detector, an infrared interrogator, a radio frequency (RF) transceiver that interrogates SDV on-board computers on other SDVs, etc.

As described in block 508, one or more processors then issue spatial separation instructions to a control mechanisms controller (e.g., SDV control mechanisms controller 303 shown in FIG. 3) on the SDV to adjust a spacing (spatial separation) between the SDV and the other vehicle based on the emotional state descriptor for said at least one occupant of the SDV. For example, if the emotional state of the occupant(s) is anxiety beyond a certain predefined level, then the spatial separation is adjusted until the anxiety level of the occupant(s) drops below that predefined level. The level of anxiety is determined by inputs from the occupant(s) (see FIG. 6) and/or by interpreting outputs from biometric sensors (e.g., biometric sensors that measure physiological responses within the occupants' bodies, photo image interpretation that identifies certain known facial expressions that express certain levels of fear, calm, anxiety, etc.).

In one embodiment of the present invention, the emotional state of the occupant(s) of the SDV are re-evaluated after the spatial separation between the SDV and the other vehicle is adjusted (e.g., lengthened). If the emotional states are still beyond the predefined level, then additional spacing is added until the occupants are comfortable (according to their subjective inputs and/or according to readings taken from biometric sensors).

The flow chart depicted in FIG. 5 ends at terminator block 510.

In one embodiment of the present invention, a vehicle interrogator (e.g., SDV on-board computer 301 shown in FIG. 3 being within SDV 202c shown in FIG. 2) detects that the other vehicle (e.g., vehicle 206 in FIG. 2) is a non-autonomous vehicle that is being operated by a human driver. The control mechanisms controller (e.g., SDV control mechanisms controller 303 shown in FIG. 3) within the SDV (e.g., SDV 202c) then further adjusts the spatial separation between the SDV 202c and the other vehicle 206 based on detecting that the human driver is operating the other vehicle. That is, the SDV on-board computer 301 within SDV 202c may display (e.g., on SDV display 311 shown in FIG. 3) a message indicating that vehicle 206 in FIG. 2 is being driven by a human. As such, rather than cause further consternation to the occupant(s) of SDV 202c (who now know that the operation of vehicle 206 is less likely to be predictable than if vehicle 206 was an SDV operating in autonomous mode), the system directs the SDV control mechanisms controller 303 to adjust operation of the set of SDV vehicular physical control mechanisms 305 to slow SDV 202c, thus providing more spatial separation between SDV 202c and vehicle 206.

In one embodiment of the present invention, the vehicle detector on the SDV detects a size of the other vehicle. Based on this detection, the control mechanisms controller further adjusts the spatial separation between the SDV and the other vehicle based on a field of view for the occupants in the SDV that is blocked by the size of the other vehicle. For example, assume that SDV 202a is tailgating SDV 204a as shown in FIG. 2. If SDV 202a and SDV 204a are both small automobiles, then the field of view of occupants of either SDV 202a or SDV 204a is not obstructed.

However, assume now that SDV 204a is a large truck and SDV 202a is a small sports car. In this scenario, the occupants of SDV 202a are likely to be unable to see anything in front of SDV 204a, as well as objects to the side of SDV 204a. This lack of vision (i.e., blocking the field of view) of the occupants of the SDV 202a is likely to increase their discomfort, due to a feeling of being closed in, as well as a legitimate concern about not being able to see unexpected items in front of or to the side of SDV 204a. Thus, the SDV control mechanisms controller 303 within SDV 202a responds by slowing SDV 202a down, thus opening up the field of view of the occupants of SDV 202a.

In an embodiment of the present invention, a weighted voting system is used to weight various variables used in making the decisions regarding how much spacing is afforded around an SDV. Such inputs may include a level of anxiety or other emotional discomfort being felt by various occupants of an SDV, which provides a weighting for such factors. For example, if all occupants of an SDV feel moderately uncomfortable due to the spacing between the SDV in which they are riding and other vehicles, then a certain weighted sum will be determined, which may be enough to cause the SDV to slow down in order to provide a greater spatial separation from the other vehicle. Alternatively, if all but one of the occupants are feeling comfortable with the spatial separation between the SDV in which they are riding and another vehicle, but the remaining occupant is feeling highly anxious because of this spatial separation, then the feelings of the last person may be weighted greatly enough (based on the level of his/her discomfort, as derived by processes described above) to cause a weighted sum to be significant to cause the SDV to slow down in order to provide a greater spatial separation from the other vehicle. The emotion level inputs are (I1, I2, . . . , IN), where "N" denotes the total number of inputs. An input's weight (w) is how significant the input level is (i.e., how significant (weighted) the input is). A quota (q) is the minimum number of votes (e.g., weighted inputs from the occupants) required to "pass a motion", which in this case refers to a decision made to adjust the spatial separation between the SDV in which the occupants are riding and another vehicle.

Thus, in one embodiment of the present invention, multiple occupants are within the SDV, and one or more processors receive a weighted emotional state descriptor for each of the multiple occupants within the SDV. The processor(s) determine a weighted average emotional state descriptor for the multiple occupants within the SDV. The control mechanisms controller then further adjusts the spatial separation between the SDV and the other vehicle based on the weighted average emotional state descriptor for the multiple occupants within the SDV.

In one embodiment of the present invention, traffic sensors (e.g., traffic sensors 253 shown in FIG. 2) receive a traffic level descriptor of a traffic level on the roadway (e.g., roadway 200 shown in FIG. 2). The control mechanisms controller then further adjusts the spatial separation instructions used to adjust the spatial separation between the SDV and the other vehicle(s) based on the traffic level on the roadway. For example, if traffic is heavy on the roadway 200 shown in FIG. 2, then the SDV control mechanisms controller 303 (shown in FIG. 3) within the SDV 302 may increase the amount of spatial separation around the SDV 302, since the heavy traffic is likely to make the occupants of the SDV 302 more nervous than if there was only light traffic on the roadway 200.

In one or more embodiments of the present invention, adjusting the spatial separation between the SDV and another vehicle is partially dependent on the types of vehicles involved. For example, assume that vehicle 202*a* shown in FIG. 2 has characteristics (e.g., make, model, size, etc.) found in other members of a cohort of vehicles. Assume that this characteristic/trait affects the vehicles' ability to respond to emergency situations (such as obstacles in the road) when operating in autonomous mode. Assume further that historical data shows that these cohort members (e.g., particular makes and models of SDVs) have a history of fewer accidents when a certain minimum spatial separation from other vehicles is maintained at all times. As such, the system (e.g., SDV on-board computer 301 shown in FIG. 3) will automatically maintain this minimum spatial separation between the SDV and other vehicles.

In one or more embodiments, the present invention is implemented in a cloud environment. It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
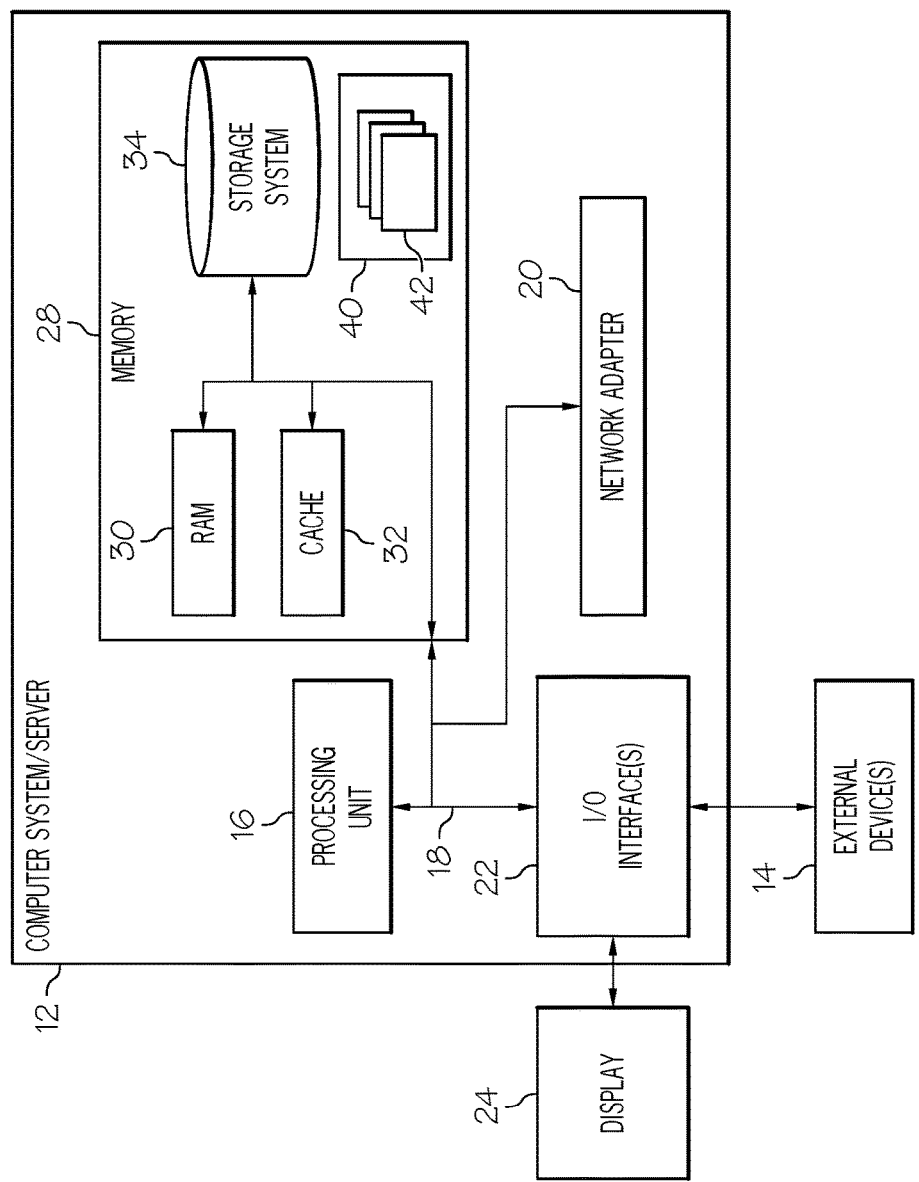
FIG. 7 depicts a cloud computing node according to an embodiment of the present disclosure.

Referring now to FIG. 7, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 8:
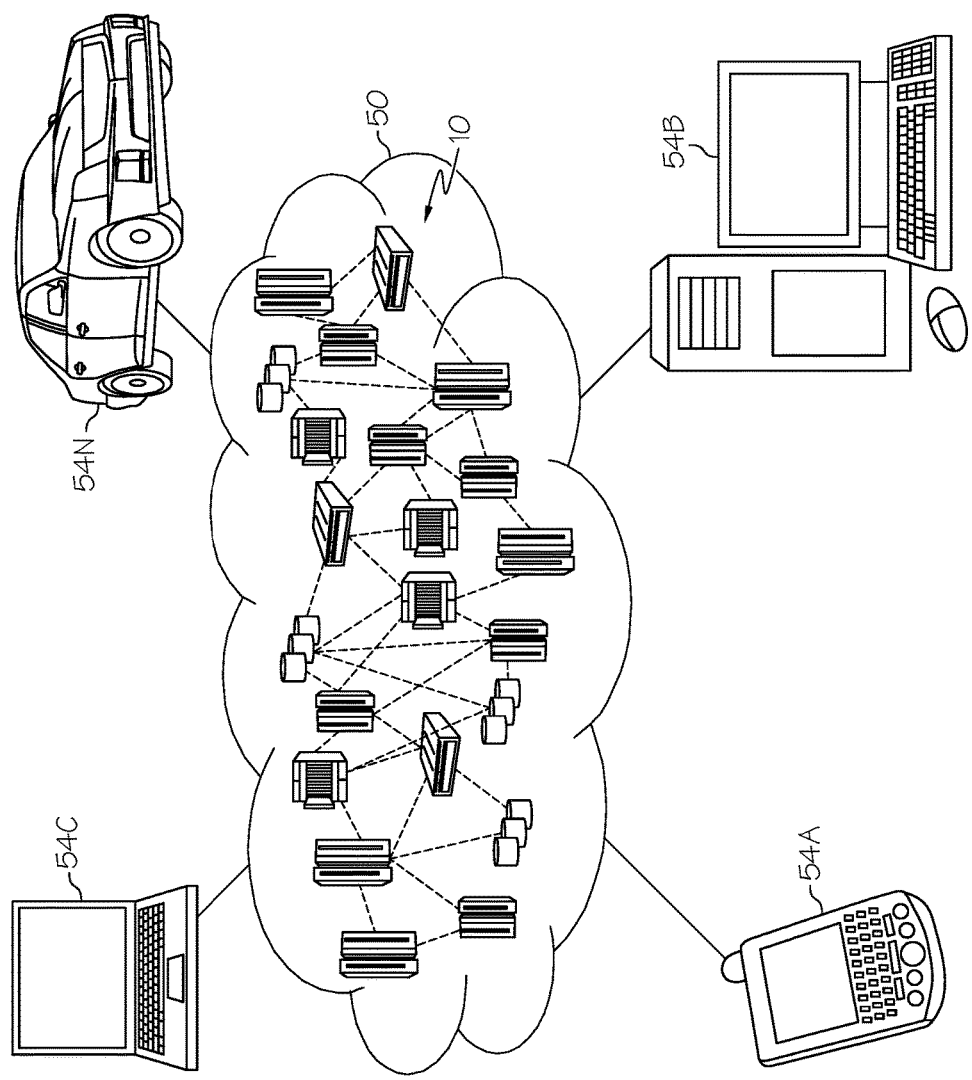
FIG. 8 depicts a cloud computing environment according to an embodiment of the present disclosure.

Referring now to FIG. 7, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
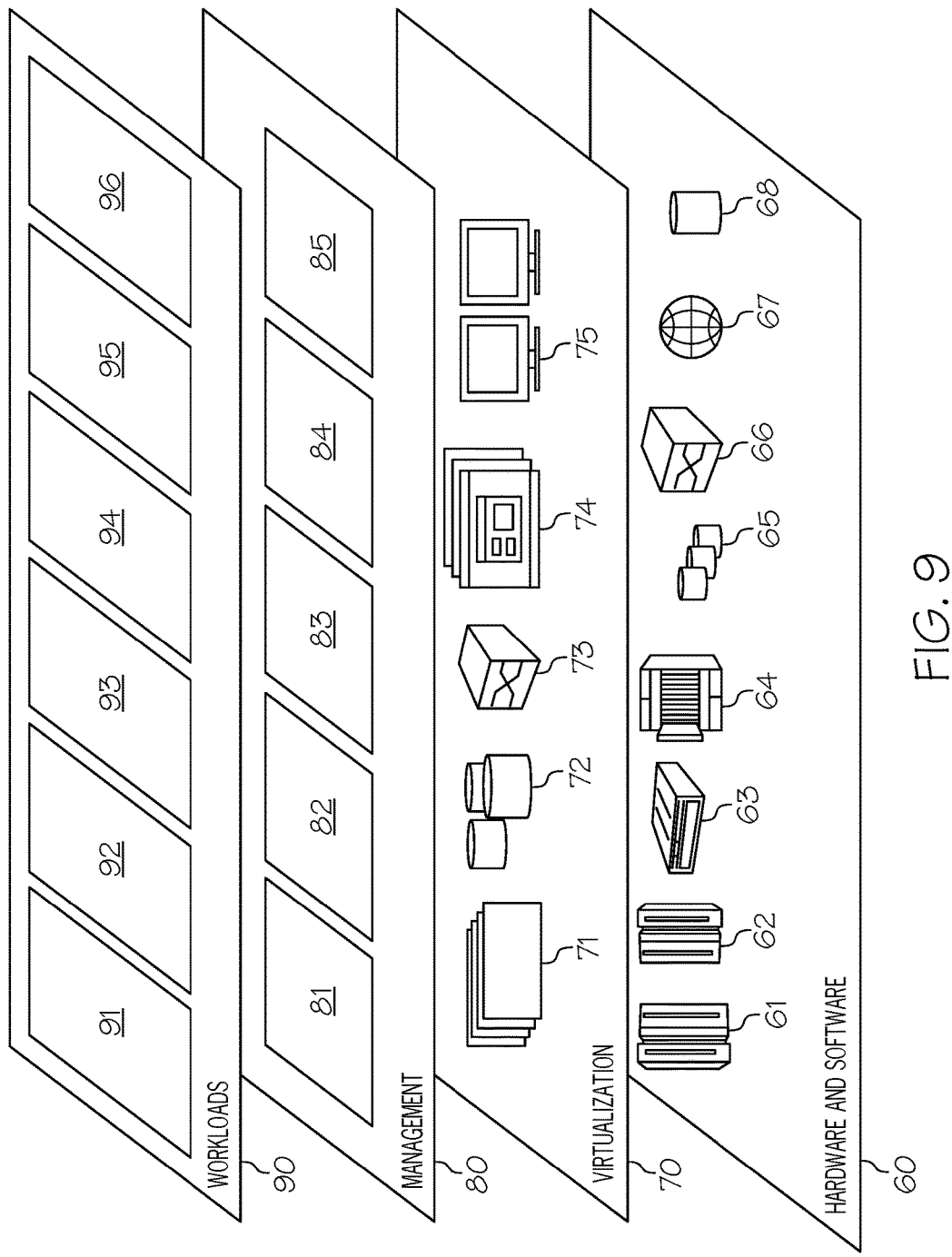
FIG. 9 depicts abstraction model layers according to an embodiment of the present disclosure.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and self-driving vehicle control processing 96 (for controlling spatial distances between vehicles as described herein).

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of various embodiments of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

Any methods described in the present disclosure may be implemented through the use of a VHDL (VHSIC Hardware Description Language) program and a VHDL chip. VHDL is an exemplary design-entry language for Field Programmable Gate Arrays (FPGAs), Application Specific Integrated Circuits (ASICs), and other similar electronic devices. Thus, any software-implemented method described herein may be emulated by a hardware-based VHDL program, which is then applied to a VHDL chip, such as a FPGA.

Having thus described embodiments of the present invention of the present application in detail and by reference to illustrative embodiments thereof, it will be apparent that modifications and variations are possible without departing from the scope of the present invention defined in the appended claims.

What is claimed is:

1. A computer-implemented method for automatically providing spatial separation between a self-driving vehicle (SDV) operating in an autonomous mode and another vehicle on a roadway, the computer-implemented method comprising:
    receiving, by one or more processors, an emotional state descriptor for at least one occupant in a self-driving vehicle (SDV);
    determining, by one or more processors, an emotional state of said at least one occupant in the SDV based on the emotional state descriptor;
    detecting, by a vehicle detector on the SDV, another vehicle within a predefined proximity of the SDV;
    detecting, by the vehicle detector on the SDV, a size of the other vehicle;
    determining, by a control mechanisms controller, that a field of view for the occupants in the SDV is blocked by the size of the other vehicle; and
    adjusting, by one or more processors, a spatial separation between the SDV and the other vehicle based on the emotional state of said at least one occupant in the SDV and the field of view for the occupants in the SDV that is blocked by the size of the other vehicle.

2. The computer-implemented method of claim 1, further comprising:
    receiving, by one or more processors, the emotional state descriptor for said at least one occupant in the SDV from an input device, wherein the input device receives the emotional state descriptor that is manually input by said at least one occupant.

3. The computer-implemented method of claim 1, further comprising:
    receiving, by one or more processors, the emotional state descriptor for said at least one occupant in the SDV from a biometric sensor within a cabin of the SDV, wherein the biometric sensor detects an emotional state of said at least one occupant.

4. The computer-implemented method of claim 1, wherein multiple occupants are within the SDV, and wherein the computer-implemented method further comprises:
    receiving, by one or more processors, a weighted emotional state descriptor for each of the multiple occupants within the SDV, wherein a weighting of the emotional state descriptor for each of the multiple occupants is based on an intensity level of an emotional state that is described by the emotional state descriptor;
    determining, by one or more processors, a weighted average emotional state descriptor for the multiple occupants within the SDV; and
    further adjusting, by the control mechanisms controller, the spatial separation between the SDV and the other vehicle based on the weighted average emotional state descriptor for the multiple occupants within the SDV.

5. The computer-implemented method of claim 1, further comprising:
    receiving, from traffic sensors, a traffic level descriptor of a traffic level on the roadway; and
    further adjusting, by the control mechanisms controller, the spatial separation instructions based on the traffic level on the roadway.

6. The computer-implemented method of claim 1, wherein the emotional state descriptor describes an emotional state for the at least one occupant in the SDV that is affected by the spatial separation between the SDV and the other vehicle.

7. The computer-implemented method of claim 1, wherein the emotional state descriptor for said at least one occupant in the SDV is from a group consisting of being happy, angry, nervous and sleepy.

8. A computer program product for automatically providing spatial separation between a self-driving vehicle (SDV) operating in an autonomous mode and another vehicle on a roadway, the computer program product comprising a non-transitory computer readable storage medium having program code embodied therewith, the program code readable and executable by a processor to perform a method comprising:
- receiving an emotional state descriptor for at least one occupant in a self-driving vehicle (SDV);
- detecting another vehicle within a predefined proximity of the SDV;
- detecting a size of the other vehicle;
- determining that a field of view for the occupants in the SDV is blocked by the size of the other vehicle; and
- adjusting a spatial separation between the SDV and the other vehicle based on the emotional state descriptor for said at least one occupant in the SDV and the field of view for the occupants in the SDV that is blocked by the size of the other vehicle.

9. The computer program product of claim 8, wherein the method further comprises:
- receiving the emotional state descriptor for said at least one occupant in the SDV from an input device, wherein the input device receives the emotional state descriptor as an input from said at least one occupant.

10. The computer program product of claim 8, wherein the method further comprises:
- receiving the emotional state descriptor for said at least one occupant in the SDV from a biometric sensor within a cabin of the SDV, wherein the biometric sensor detects an emotional state of said at least one occupant.

11. The computer program product of claim 8, wherein the method further comprises:
- detecting that the other vehicle is a non-autonomous vehicle that is being operated by a human driver; and
- issuing additional spatial separation instructions to a control mechanisms controller on the SDV to further adjust the spatial separation between the SDV and the other vehicle based on detecting that the human driver is operating the other vehicle.

12. The computer program product of claim 8, wherein the SDV is a first SDV that is following the other vehicle, and wherein the method further comprises:
- determining that the other vehicle is another SDV;
- determining that the first SDV is unable to increase the spatial separation between the first SDV and the other vehicle; and
- transmitting, to the other vehicle, instructions to speed up in order to increase the spatial separation between the first SDV and the other vehicle.

13. The computer program product of claim 8, wherein multiple occupants are within the SDV, and wherein the method further comprises:
- receiving a weighted emotional state descriptor for each of the multiple occupants within the SDV;
- determining a weighted average emotional state descriptor for the multiple occupants within the SDV; and
- issuing additional spatial separation instructions to a control mechanisms controller on the SDV to further adjust the spatial separation between the SDV and the other vehicle based on the weighted average emotional state descriptor for the multiple occupants within the SDV.

14. The computer program product of claim 8, wherein the method further comprises:
- receiving, from traffic sensors, a traffic level descriptor of a traffic level on the roadway; and
- issuing additional spatial separation instructions to a control mechanisms controller on the SDV to further adjust the spatial separation between the SDV and the other vehicle based on the traffic level on the roadway.

15. A computer system comprising:
- a processor, a computer readable memory, and a non-transitory computer readable storage medium;
- first program instructions to receive an emotional state descriptor for at least one occupant in a self-driving vehicle (SDV), wherein the emotional state descriptor for said at least one occupant in the SDV is received as a text input from said at least one occupant into an input device;
- second program instructions to detect another vehicle within a predefined proximity of the SDV;
- third program instructions to detect a size of an other vehicle;
- fourth program instructions to determine that a field of view for the occupants in the SDV is blocked by the size of the other vehicle; and
- fifth program instructions to adjust a spatial separation between the SDV and the other vehicle based on the emotional state descriptor for said at least one occupant in the SDV and the field of view for the occupants in the SDV that is blocked by the size of the other vehicle; and wherein the first, second, third, fourth, and fifth program instructions are stored on the non-transitory computer readable storage medium for execution by one or more processors via the computer readable memory.

16. The computer system of claim 15, further comprising:
- sixth program instructions to further adjust the spatial separation between the SDV and the other vehicle based on an accident history of a make and model of the SDV; and wherein the sixth program instructions are stored on the non-transitory computer readable storage medium for execution by one or more processors via the computer readable memory.

17. The computer system of claim 15, further comprising:
- sixth program instructions to further receive the emotional state descriptor for said at least one occupant in the SDV from a biometric sensor within a cabin of the SDV, wherein the biometric sensor detects an emotional state of said at least one occupant; and wherein the sixth program instructions are stored on the non-transitory computer readable storage medium for execution by one or more processors via the computer readable memory.

18. The computer system of claim 15, further comprising:
- sixth program instructions to detect that the other vehicle is a non-autonomous vehicle that is being operated by a human driver; and
- seventh program instructions to issue additional spatial separation instructions to a control mechanisms controller on the SDV to further adjust the spatial separation between the SDV and the other vehicle based on detecting that the human driver is operating the other vehicle; and wherein the sixth and seventh program instructions are stored on the non-transitory computer readable storage medium for execution by one or more processors via the computer readable memory.

* * * * *